US010383849B2

(12) United States Patent
de Jong et al.

(10) Patent No.: US 10,383,849 B2
(45) Date of Patent: Aug. 20, 2019

(54) USE OF AN ACETYLCHOLINESTERASE INHIBITOR AND IDALOPIRDINE FOR REDUCING FALLS IN PARKINSON'S DISEASE PATIENTS

(71) Applicant: H. Lundbeck A/S, Valby (DK)

(72) Inventors: Inge E. M. de Jong, Valby (DK); Aaron Kucinski, Ann Arbor, MI (US); Martin Sarter, Ann Arbor, MI (US)

(73) Assignee: H. LUNDBECK A/S, Valby (DK)

( * ) Notice: Subject to any disclaimer, the term of this patent is extended or adjusted under 35 U.S.C. 154(b) by 0 days.

(21) Appl. No.: 15/496,159

(22) Filed: Apr. 25, 2017

(65) Prior Publication Data
US 2017/0304267 A1 Oct. 26, 2017

Related U.S. Application Data

(60) Provisional application No. 62/363,463, filed on Jul. 18, 2016.

(30) Foreign Application Priority Data

Apr. 26, 2016 (DK) ................................. 2016 00248

(51) Int. Cl.
| | | |
|---|---|---|
| *A61K 31/27* | (2006.01) | |
| *A61K 31/55* | (2006.01) | |
| *A61K 45/06* | (2006.01) | |
| *A61K 31/445* | (2006.01) | |
| *A61K 31/4045* | (2006.01) | |

(52) U.S. Cl.
CPC .......... *A61K 31/4045* (2013.01); *A61K 31/27* (2013.01); *A61K 31/445* (2013.01); *A61K 31/55* (2013.01); *A61K 45/06* (2013.01)

(58) Field of Classification Search
CPC ................................ A61K 31/27; A61K 31/55
See application file for complete search history.

(56) References Cited

U.S. PATENT DOCUMENTS

2006/0270709 A1* 11/2006 Gray .................. A61K 31/4412
514/332
2014/0073681 A1* 3/2014 Schmidt ............. A61K 31/4045
514/415

2015/0320742 A1* 11/2015 Chuang .................. A61K 31/00
514/221

FOREIGN PATENT DOCUMENTS

WO WO 2000/012623 3/2000
WO WO 2002/078693 10/2002

OTHER PUBLICATIONS

ClinicalTrials.gov (NCT01019421) 2009-2012.*
Hausdorff (Chaos (2009) 19(2).*
Kucinski et al. (european J. of Neurosci, 1-15, (2016).*
Allcock, L.M., et al. (2009) "Impaired Attention Predicts Falling in Parkinson's Disease," Parkinsonism and Related Disorders 15:110-115.
Amboni, M., et al. (2013) "Cognitive Contributions to Gait and Falls: Evidence and Implications," Mov. Disord. 28(11):1520-1533.
Baker, S.P., et al. (1985) "Fall Injuries in the Elderly," Clin. Geriatr. Med. 1(3):501-512 (Abstract Only).
Balash, Y., et al. (2005) "Falls in Outpatients with Parkinson's Disease: Frequency, Impact and Identifying Factors," J. Neurol. 252:1310-1315.
Bohnen, N.I., et al. (2009) "Cholinergic Denervation Occurs Early in Parkinson Disease," Neurology 73:256-257.
Bohnen, N.I., et al. (2009) "History of Falls in Parkinson Disease is Associated with Reduced Cholinergic Activity," Neurology 73:1670-1676.
Bohnen, N.I., et al. (2011) "The Cholinergic System and Parkinson Disease," Behav. Brain Res. 221(2):564-573.
Bohnen, N.I., et al. (2013) "Gait Speed in Parkinson Disease Correlates with Cholinergic Degeneration," Neurology 81:1611-1616.
Bohnen, N.I., et al. (2014) "Extra-Nigral Pathologies are Common in Parkinson Disease with Freezing of Gait: An In Vivo PET Study," Mov. Disord. 29(9):1118-1124.
Brown, L.A., et al. (1999) "Attentional Demands and Postural Recovery: The Effects of Aging," J. Gerontology: Med. Sci. 54A(4):M165-M171.
Cameron, I.D., et al. (2012) "Interventions for Preventing Falls in Older People in Care Facilities and Hospitals," Cochrane Database Syst. Rev. 12:CD005465.
Chung, K.A., et al. (2010) "Effects of a Central Cholinesterase Inhibitor on Reducing Falls in Parkinson Disease," Neurology 75(14): 1263-1269.
Dellinger, A.M., et al. (2006) "The Injury Problem Among Older Adults: Mortality, Morbidity and Costs," J. Safety Res. 37:519-522.
Ensrud, K.E., et al. (2003) "Central Nervous System Active Medication and Risk for Fractures in Older Women," Arch. Intern. Med. 163:949-957.
Gillespie, L.D., et al. (2012) "Interventions for Preventing Falls in Older People Living in the Community," Cochrane Database Syst. Rev. 9:CD007146.
Gritton, H.J., et al. (2016) "Cortical Cholinergic Signaling Controls the Detection of Cues," PNAS 113(8):E1089-E1097.

(Continued)

*Primary Examiner* — Shirley V Gembeh
(74) *Attorney, Agent, or Firm* — Wilmer Cutler Pickering Hale and Dorr LLP

(57) ABSTRACT

The present invention relates to the use of an acetylcholinesterase inhibitor and idalopirdine for reducing falls in patients suffering from a CNS disease, in particular patients with Parkinson's disease, wherein balance, gait or movement is impaired.

17 Claims, 7 Drawing Sheets

(56) References Cited

OTHER PUBLICATIONS

Hasselmo, M.E., et al. (2011) "Modes and Models of Forebrain Cholinergic Neuromodulation of Cognition," Neuropsychopharmacol. 36:52-73.

Hausdorff, J.M., et al. (2006) "A Common Cognitive Profile in Elderly Fallers and in Patients with Parkinson's Disease: The Prominence of Impaired Executive Function and Attention," Exp. Aging Res. 32(4):411-429.

Henderson, E.J., et al. (2016) "Rivastigmine for Gait Stability in Patients with Parkinson's Disease (ReSPonD): A Randomised, Double-Blind, Placebo-Controlled, Phase 2 Trial," Lancet Neurol. 15:249-258.

Herrik, K.F., et al. (2016) "The 5-$HT_6$ Receptor Antagonist Idalopirdine Potentiates the Effects of Acetylcholinesterase Inhibition on Neuronal Network Oscillations and Extracellular Acetylcholine Levels in the Rat Dorsal Hippocampus," Neuropharmacol. 107:351-363.

Kucinski, A., et al. (2016) "Reducing Falls in Parkinson's Disease: Interactions Between Donepezil and the 5-$HT_6$ Receptor Antagonist Idalopirdine on Falls in a Rat Model of Impaired Cognitive Control of Complex Movements," Eur. J. Neurosci. 45:217-231.

Langston, J.W. (2006) "The Parkinson's Complex: Parkinsonism is Just the Tip of the Iceberg," Annals of Neurology 59(4):591-596.

LaPointe, L.L., et. al. (2010) "Talking While Walking: Cognitive Loading and Injurious Falls in Parkinson's Disease," Int'l J. Speech-Language Pathology 12(5):455-459.

Montero-Odasso, M., et al. (2012) "Gait and Cognition: A Complementary Approach to Understanding Brain Function and the Risk of Falling," J. Am. Geriatr. Soc. 60(11):2127-2136.

Partial International Search Report and Written Opinion of the International Searching Authority PCT/EP2017/059739 (2017) (19 pages).

Shen, X., et al. (2015) "Effects of Exercise on Falls, Balance, and Gait Ability in Parkinson's Disease: A Meta-analysis," Neurorehabilitation and Neural Repair 30(6):512-527.

Theill, N., et al. (2011) "Simultaneously Measuring Gait and Cognitive Performance in Cognitively Healthy and Cognitively Impaired Older Adults: The Basel Motor-Cognition Dual-Task Paradigm," J. Am. Geriatr. Soc. 59:1012-1018.

Tinetti, M.E., et al. (1988) "Risk Factors for Falls Among Elderly Persons Living in the Community," N. Engl. J. Med. 319(26):1701-1707.

Van der Marck, M.A., et al. (2014) "Consensus-Based Clinical Practice Recommendations for the Examination and Management of Falls in Patients with Parkinson's Disease," Parkinsonism and Related Disorders 20:360-369.

Wood, B.H., et al. (2002) "Incidence and Prediction of Falls in Parkinson's Disease: A Prospective Multidisciplinary Study," J. Neurol. Neurosurg. Psychiatry 72:721-725.

Woollacott, M., et al. (2002) "Attention and the Control of Posture and Gait: A Review of an Emerging Area of Research," Gait and Posture 16:1-14.

Yarnall, A. et al.(2011) "The Interplay of Cholinergic Function, Attention, and Falls in Parkinson's Disease," Mov. Disord. 26(14):2496-2503.

Yogev, G., et al. (2008) "The Role of Executive Function and Attention in Gait," Mov. Disord. 23(3):329-472.

Arnt, J., et al., "Lu AE58054, a 5-$HT_6$ antagonist, reverses cognitive impairment induced by subchronic phencyclidine in a novel object recognition test in rats," International Journal of Neuropsychopharmacology, vol. 13, pp. 1021-1033 (Jun. 23, 2010).

International Search Report and Written Opinion dated Oct. 16, 2017 by European Patent Office in International Patent Application No. PCT/EP2017/059739 (27 total pages).

* cited by examiner

USE OF AN ACETYLCHOLINESTERASE INHIBITOR AND IDALOPIRDINE FOR REDUCING FALLS IN PARKINSON'S DISEASE PATIENTS

CROSS-REFERENCE TO RELATED APPLICATIONS

This application is claims priority to U.S. Provisional Patent Application No. 62/363,463 (filed on Jul. 18, 2016), and Denmark Patent Application No. PA201600248 (filed on Apr. 26, 2016), each of which applications is herein incorporated by reference in its entirety.

FIELD OF THE INVENTION

The present invention relates to the use of an acetylcholinesterase inhibitor and idalopirdine for reducing falls in elderly patients, such as elderly patients with Parkinson's disease. The invention further relates to the combination of an acetylcholinesterase inhibitor and idalopirdine for reducing falls in patients suffering from Parkinson's disease.

BACKGROUND OF THE INVENTION

Falls are a leading cause of death in the elderly and, in a majority of patients with Parkinson's disease (PD), the leading levodopa-insensitive cause of hospitalization and longterm care. Falling in PD has been attributed to degeneration of forebrain cholinergic neurons that, in interaction with striatal dopamine losses, impairs the cognitive control of balance, gait and movement.

In addition to the disease characterizing motor symptoms reflecting primarily striatal dopamine loss, prominent autonomic, behavioral and cognitive symptoms, including a propensity for falls, indicate that Parkinson's disease (PD) is based on more widespread, multisystemneurodegenerative processes[1]. Falls in PD patients[2,3] and also in the healthy elderly[4] are often disabling events[5,6]. Both exercise-based programs[7-9] and the treatment with acetylcholinesterase inhibitors[10,11] reduce fall rates in the elderly and PD patients, though an umnet need to further reduce fall propensity remains.

Although falls in patients are associated with numerous risk factors[12-14] impairments in the attentional supervision of movement are a major contributing factor, specifically when unfamiliar surfaces and obstacles or secondary tasks challenge gait, balance, and movement control[15-22]. Gait, balance and movement errors normally evoke compensatory attentional control. However, as the disease process also impacts the brain's attention systems, such compensatory deployment of attentional resources is increasingly unavailable for rescuing movement and preventing falls. Consistent with this view, both degeneration of the basal forebrain (BF) cholinergic projections to telencephalic and thalamic regions—a major attention system of the brain[23,24]—and of the cholinergic brain stem projections to thalamus and basal ganglia, correlate with low gait speed, freezing of gait and falls in PD patients[25-29].

Also in other CNS diseases such as Lewy Body Dementia (LBD), Parasupranuclear Palsy (PSP) and Mutli Systems Atropy (MSA) balance, gait and movement are impaired due to degeneration of cholinergic neurons[30].

From the above it is clear that there remains an unmet need for treatment for use in reducing falls in patients with Parkinson's disease as well as in patients with other CNS diseases where degeneration of cholinergic neurons leads to balance, gait and movement impairment. N-(2-(6-fluoro-1H-indol-3-yl)ethyl)-3-(2,2,3,3-tetrafluoropropoxy) benzylamine with the INN name "idalopirdine" (depicted below) is for the first time disclosed in WO 02/078693 and it is a potent and selective 5-$HT_6$ receptor antagonist which has been in clinical development for treating cognition impairment associated with schizophrenia and as a treatment for AD.

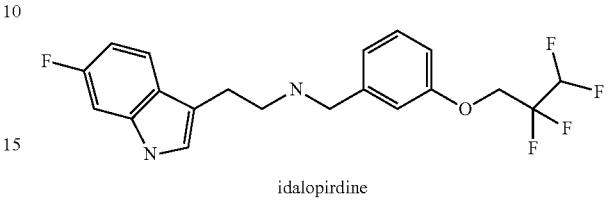

idalopirdine

In 2012, a clinical study was reported with idalopirdine used in the treatment of Alzheimer's disease (AD). Data demonstrated that Idalopirding plus 10 mg/day of donepezil significantly improved cognitive function in 278 patients with AD compared to placebo plus donepezil, when measured by AD Assessment Scale-cognitive sub-scale (ADAS-cog). Idalopirdine showed positive results in secondary endpoints including measures of global impression and daily living activities compared to donepezil treated patients. A subsequent phase III study has not bee able to confirm the results.

The results included in this patent application have partly been disclosed in an e-publication (doi: 10.111/ejn.13354, published 29 Jul. 2016)[31]. Further, the Michigan Complex Motor Control Task (MCMCT) that is used for evaluation of treatment impact on falls, gait and movement stoppages has been described in an article by Kucinski et al.[32]

SUMMARY OF THE INVENTION

The present invention relates to an 5-$HT_6$ receptor antagonist, such as idalopirdine (IDL), and an acetylcholinesterase inhibitor (AChEI), such as donepezil (DON), rivastigmine (Riva) or galantamine (GAL), for use in the treatment of Parkinson's disease by reducing falls in a patient with Parkinson's disease. The inventors of the present invention surprisingly found that co-treatment with donepezil and idalopirdine or rivastigmine and idalopirdine reduces falls in dual striatal-dopaminergic, corticalcholinergic system lesions (DL) rats. These results suggest that the co-treatment with an AChEI and a 5$HT_6$ receptor antagonist may reduce the fall propensity in PD patients, in particular in PD patients who also exhibit a propensity for relatively brief movement stoppages evoked by distractors or occurring spontaneously.

Figures 1A, 1B, 1C, 1D, 1E:
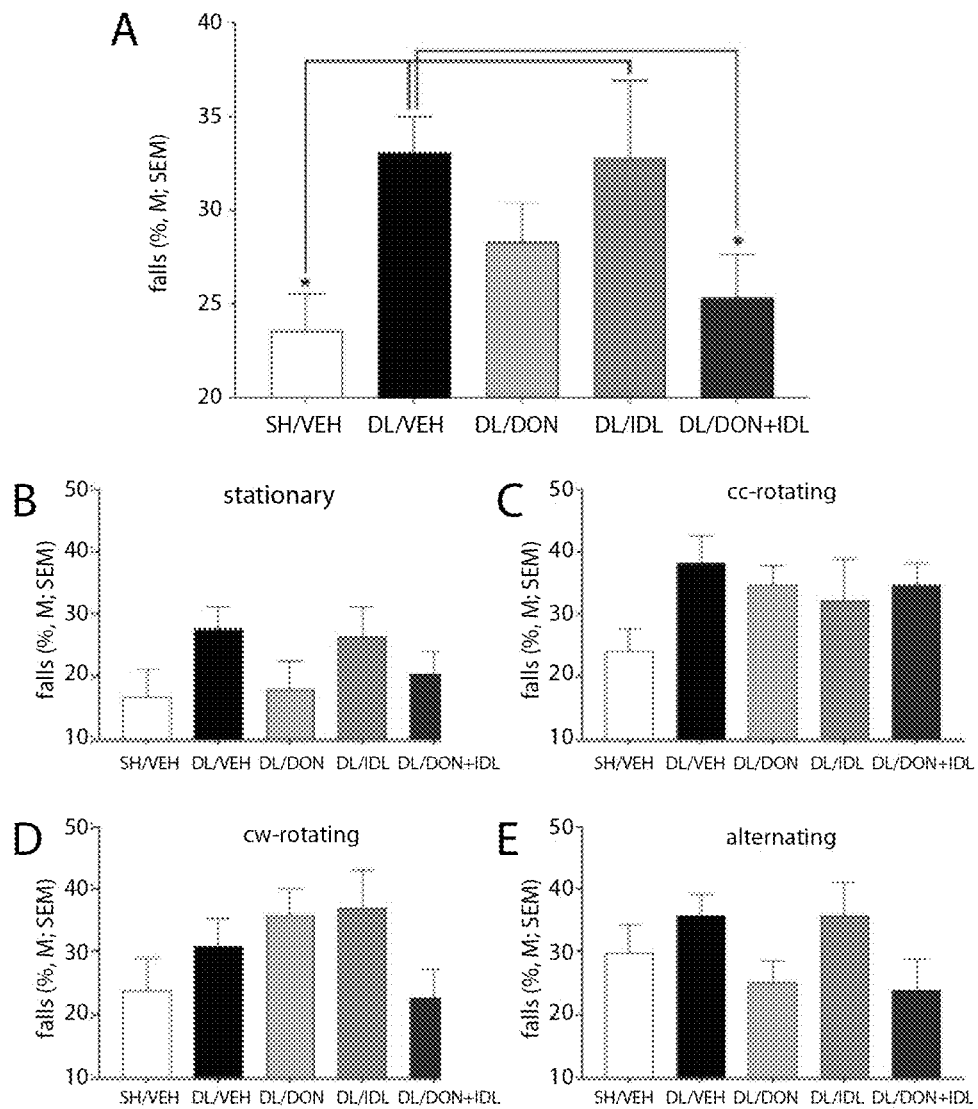
FIGS. 1A-1E.

Falls during rod traversal (N=70, n=14 per group and 7/sex). Across all testing conditions, DL rats fell more frequently than SH/VEH rats. Furthermore, compared with DL/VEH rats, treatment with DON+IDL significantly lowered fall rates (FIG. 1A). Inspection of individual testing conditions (FIGS. 1B-1E) indicated that reduction of falls associated with traversing the rod rotating in the unfamiliar clockwise (cw) direction and alternatingly rotating in the cw and counterclockwise (cc) directions contributed primarily to the overall effect of DON+IDL in DL rats. This and the following figures indicate the results of post hoc multiple comparisons that were based on significant results from ANOVAs that are described in Results (*,,*, P<0.05, 0.01, 0.001; abbreviations used in this and other figures: SH, sham-operated; DL, dual basal forebrain cholinergic and striatal dopaminergic lesions; DON, donepezil, IDL, idalopirdine, Riva, rivastigmine).

FIGS. 2A-2E.

Figures 2A, 2B, 2C, 2D, 2E:
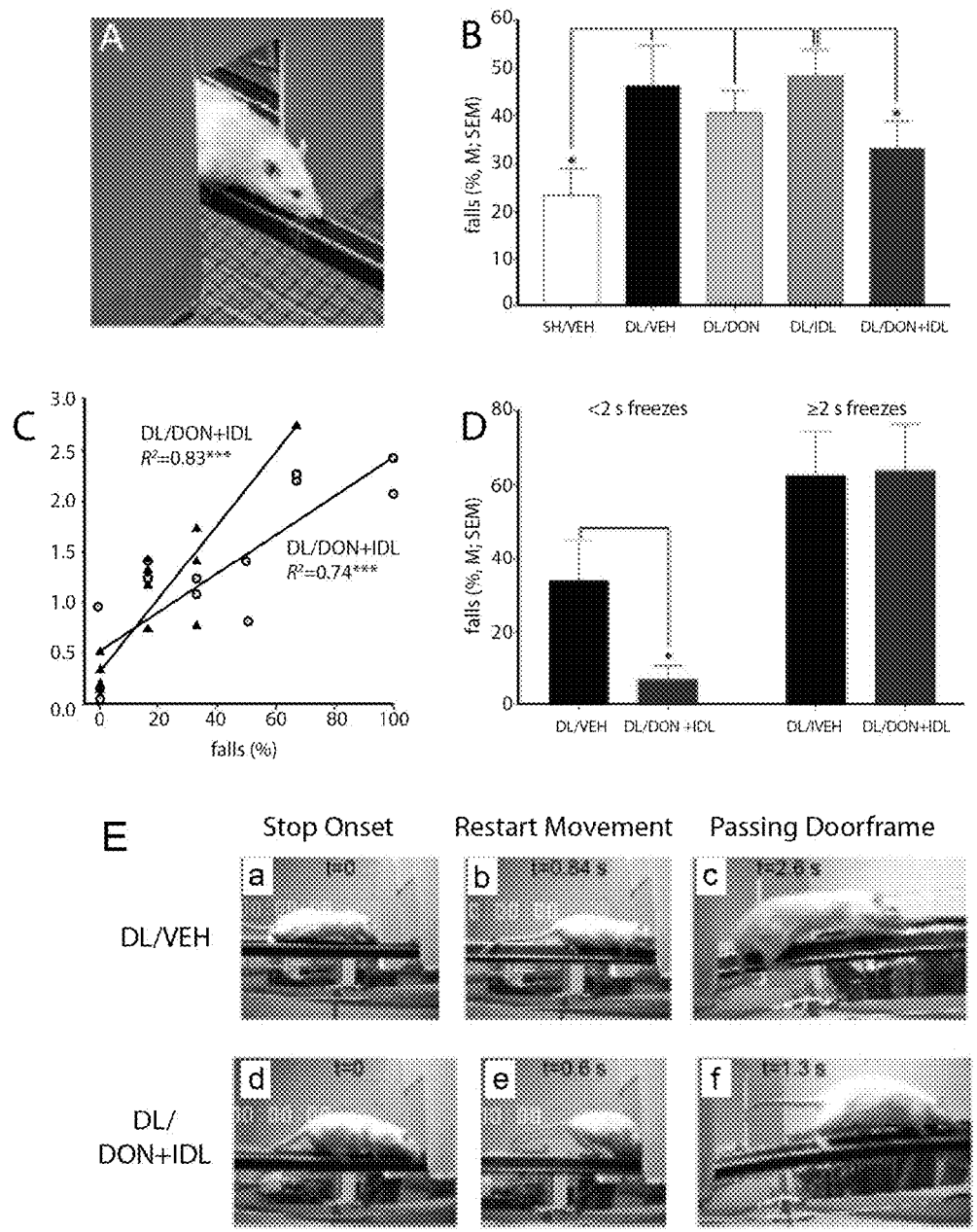

Effects of the doorframe distractor (N=70, n=14 per group and 7/sex). All DL rats, except for DL/DON+IDL rats, fell more frequently than SH/VEH rats when exposed to this passive distractor (FIGS. 2A, 2B). To gain insight into potential behavioral mechanisms mediating the effects of DON+IDL, the doorframe-associated behavior of DL/VEH and DL/DON+IDL rats was further analyzed. Doorframe-associated falls were associated with stoppage of movement or freezing of gait, as rats approached or reached the frame. Generally, longer freezes were associated with more falls (FIG. 2C) in both DL/VEH and DL/DON+IDL rats. Indeed, falls associated with longer freezes did not differ between the groups (FIG. 2D). However, DON+IDL treated rats fell significantly less frequently when freezes remained relatively short (<2 s). The proportion of short freezes itself did not differ between the groups. As illustrated in FIG. 2E, following short freezes, and even if they did not fall, DL/VEH rats resumed forward movement relatively slowly, generally with the tail positioned relatively low and with a slouched posture (note that this rat slips after passing through the door (panel a (t=0), panel b (t=0.84 s) and panel c (t=2.6 s)). In contrast, when DL/DON+IDL rats resumed forward movement, sometimes starting with a hop (as shown here), they quickly regaining regular traversal speed and fluid forward movement, with high and firm tail position and upright posture (panel d (t=0), panel e (t=0.6 s) and panel f (t=1.3 s)).

FIGS. 3A-3C.

Figures 3A, 3B, 3C:
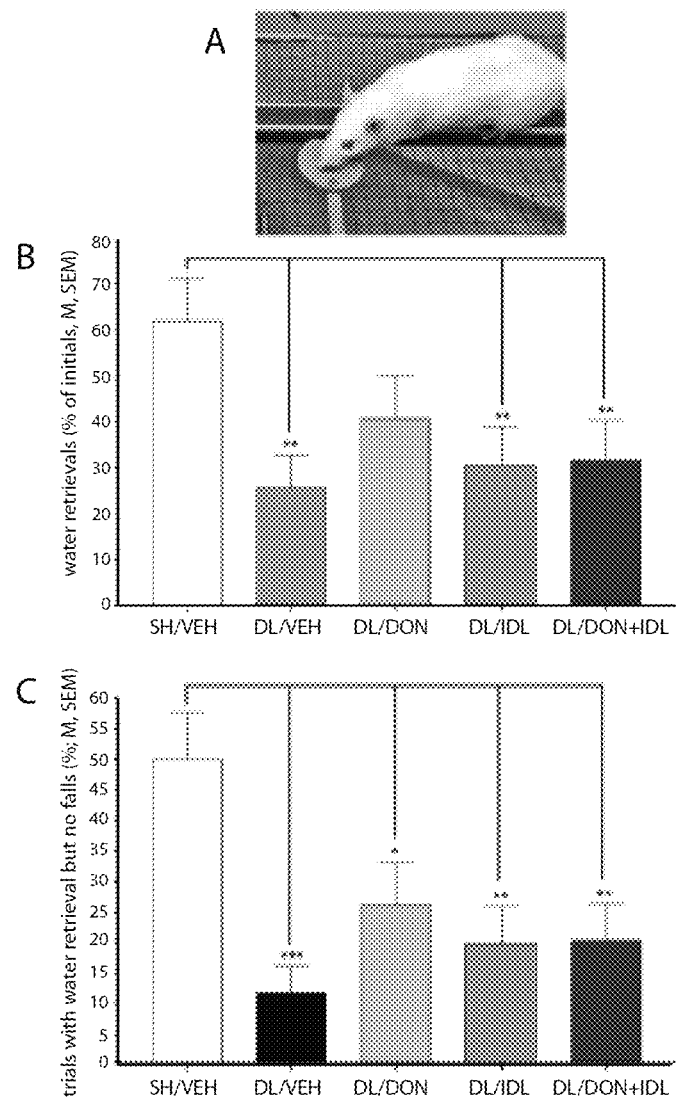
Figure 4:
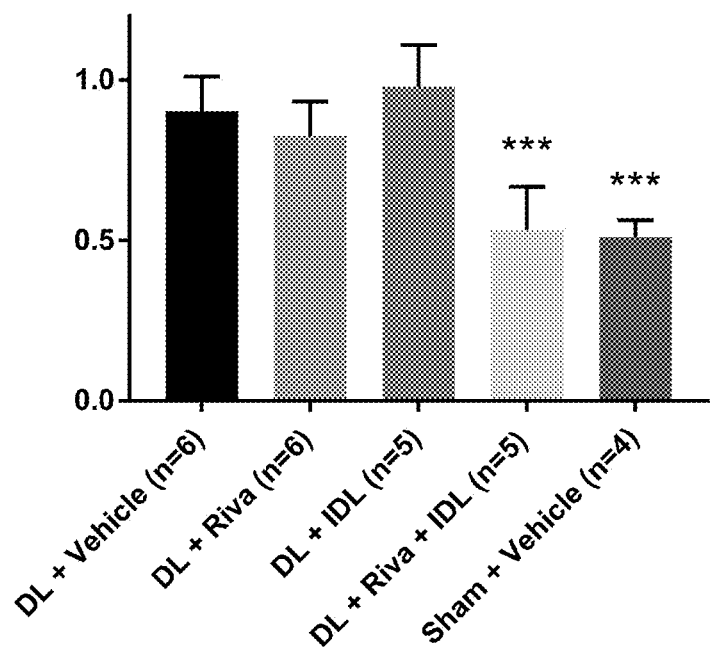
Figure 5:
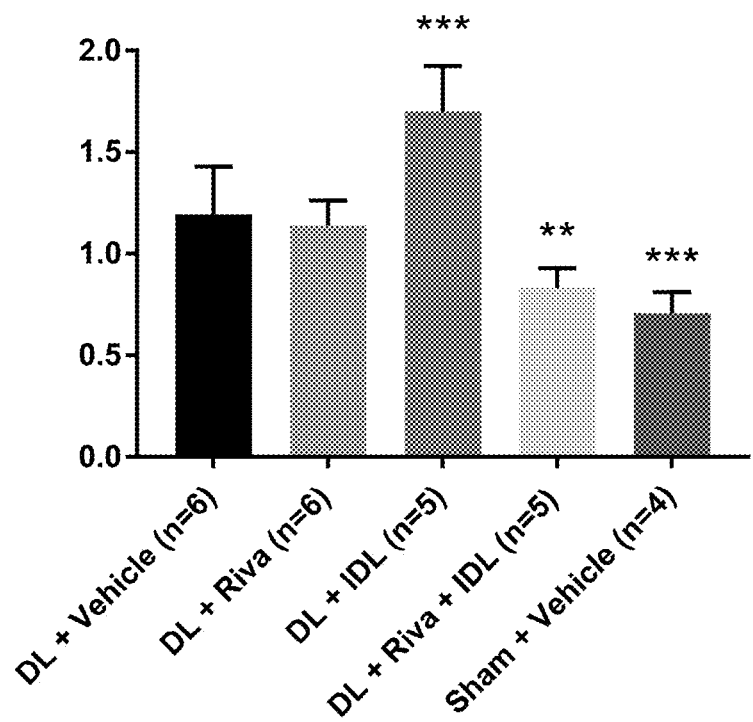
Figure 6:
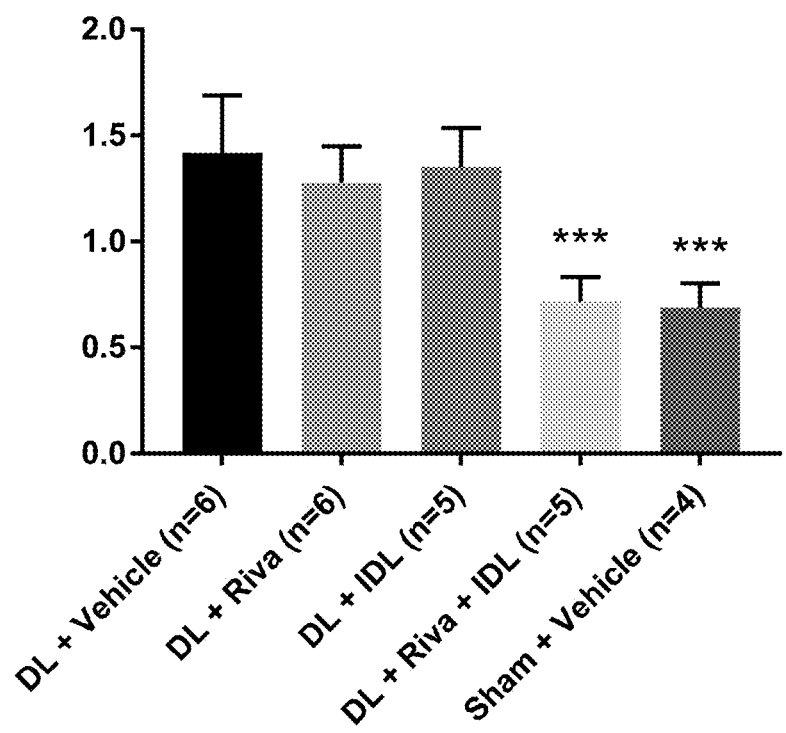
Figure 7:
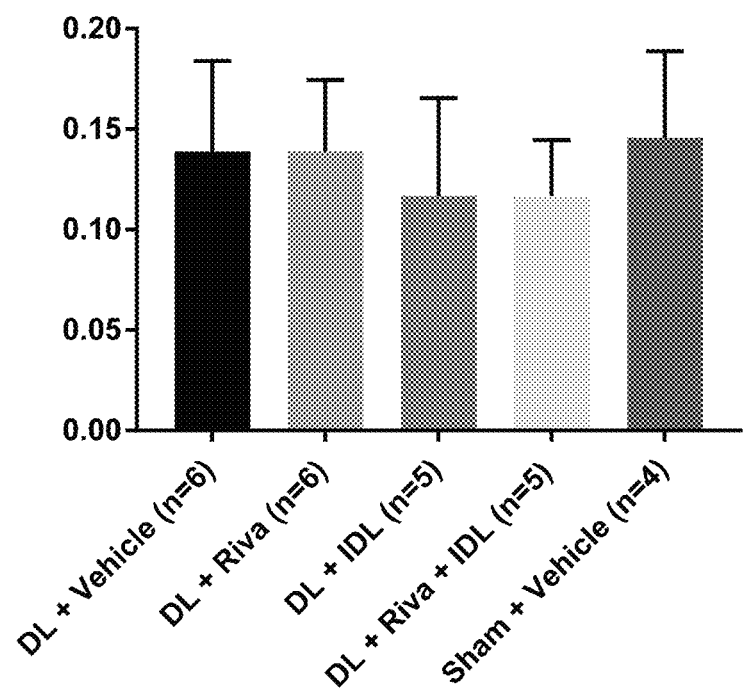

Performance on active distractor task (N=70, n=14 per group and 7/sex). To model the impact of a secondary task, water was offered as rats traversed the rotating rod (see FIG. 3A photograph; rats were water-deprived because of the parallel, daily SAT testing). DL rats were generally less likely to engage in this competing activity as indicated by lower number of attempts to retrieve the water (FIG. 3B). DL rats were also less likely to retrieve water without incurring a fall (FIG. 3C). Neither of the drug treatments (donepezil (DON) or idalopirdine (IDL) alone or in combination) did not significantly improve the performance of DL rats in the presence of this active distractor.

FIG. 4

Total number of falls combined from days 2 until 5. Shown is the total number of falls recorded (y-axis) in either dual lesion (DL) or sham operated rats after treatment with vehicle, 1 mg/kg rivastigmine, 10 mg/kg idalopirdine or the treatment combination for ten days. Bars represent mean±sem, *** P<0.001 cf. DL+Vehicle. N numbers indicated in parenthesis.

FIG. 5

Total number of falls from the alternating rod (day 5). Shown is the total number of falls recorded (y-axis) in either dual lesion (DL) or sham operated rats after treatment with vehicle, 1 mg/kg rivastigmine, 10 mg/kg idalopirdine or the treatment combination for ten days. Bars represent mean±sem, * P<0.001,  P<0.01 cf. DL+Vehicle. N numbers indicated in parenthesis.

FIG. 6

Total number of falls from the counter-clockwise rod (day 4). Shown is the total number of falls recorded (y-axis) in either dual lesion (DL) or sham operated rats after treatment with vehicle, 1 mg/kg rivastigmine, 10 mg/kg idalopirdine or the treatment combination for ten days. Bars represent mean±sem, *** P<0.001 cf. DL+Vehicle. N numbers indicated in parenthesis.

FIG. 7

Total number of falls from the stationary rod. Shown is the total number of falls recorded (y-axis) in either dual lesion (DL) or sham operated rats after treatment with vehicle, 1 mg/kg rivastigmine, 10 mg/kg idalopirdine or the treatment combination for ten days. Bars represent mean±sem, *** P<0.001 cf. DL+Vehicle. N numbers indicated in parenthesis.

DEFINITIONS

Throughout the specification, the term "idalopirdine" (sometimes abbreviated IDL) is intended to include any form of the compound, such as the free base and pharmaceutically acceptable salts. The free base and pharmaceutically acceptable salts include anhydrous forms and solvated forms such as hydrates. The anhydrous forms include amorphous and crystalline forms, and the solvates include crystalline forms. Likewise, the term "donepezil" (sometimes abbreviated DON) is intended to include any form of the compound, such as the free base and pharmaceutically acceptable salts etc.

An acetylcholinesterase inhibitor (in the present context abbreviated "AChEI") is a chemical or a drug that inhibits the acetylcholinesterase enzyme from breaking down acetylcholine, thereby increasing both the level and duration of action of the neurotransmitter acetylcholine. In the present context, examples of acetylcholinesterase inhibitors include, but are not limited to, donepezil, rivastigmine and galantamine.

Throughout the specification, the term "elderly patient" refers to a person which is at least 60 years old, such as at least 65 years old, such as at least 70, 75, 80, 85 or 90 years old.

In the present context, when idalopirdine is used in combination with an AChEI, this indicates in one embodiment that said two compounds can be administrated simultaneously for example in a pharmaceutical composition comprising both compounds. In another embodiment, when idalopirdine is used in combination with an AChEI, this indicates that said two compounds are administered separately in suitable individual pharmaceutical compositions. These individual compositions may be administered simultaneously e.g. with regular intervals once daily either morning or evening, or they may be administered independently e.g. one compound with regular intervals once daily in the morning and the other compound with regular intervals once daily in the evening.

In the present context, "Pharmaceutical composition" refers to a dose form for example an oral dose form, such as a solid oral dose form, typically tablets or capsules. "Pharmaceutical compositions of the present invention" refers to all pharmaceutical compositions covered by the claims and description.

In the present context, "pharmaceutical excipients" include e.g. inert solid diluents or fillers, sterile aqueous solutions and various organic solvents used ni pharmaceutical compositions of the present invention.

In the present context, a "unit dosage form" refers to a formulation unit of a pharmaceutical composition e.g. one tablet or one capsule.

In the present context, the "therapeutically effective amounts" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

The term "functional impairment in cholinergic neurons" is a health condition in which the normal function of the cholinergic neurons is less than full capacity.

The term "degeneration of cholinergic neurons" is a health condition in which progressive deterioration of the cholinergic neurons in the brain.

In the present context, "treatment" or "treating" is intended to indicate the management and care of a patient for the purpose of alleviating, arresting, partly arresting or delaying progress of the clinical manifestation of the disease, or curing the disease. In one aspect of the present invention, "treatment" and "treating" refers to prophylactic (preventive) treatment. In another aspect, "treatment" and "treating" refers to (curative) treatment. The patient to be treated is preferably a mammal, in particular a human being.

"DL rats" are rats that have undergone a dual striatal-dopaminergic, corticalcholinergic system lesions.

DETAILED DESCRIPTION OF THE INVENTION

The inventors of the present invention have surprisingly identified that the combination of idalopirdine and donepezil or idalopirdine and rivastigmine was able to reduce falls in an animal model indicating the potential of the combination of these two substances for therapeutic treatment in reducing falls in patients with PD and in elderly patients. In brief, the effects of donepezil (DON) and idalopirdine (IDL) were tested in rats with cortical cholinergic and striatal dopaminergic losses (DL rats) traversing rotating rods and performing the Sustained Attention Task (SAT). The main findings indicate that treatment with DON+IDL reduced falls on the rotating rod as well as falls evoked by the doorframe distractor. DON+IDL prevented falls primarily by enhancing the efficacy and vigor of the re-initiation of rotating rod traversal following relatively brief movement stoppages. DL rats treated with DON+IDL exhibited less falls while traversing the rotating rod than other DL groups, and they fell less often in association with relatively short doorframe-evoked stoppages. Further, treatment of DL rats with Riva+ IDL also showed a reduced number of falls in DL rats when compared to DL rats treated with vehicle only. See experimental section for further details.

In human fallers, as in DL rats, slow gait speed and movement stoppages, evoked by distractors or occurring without obvious causes, destabilize forward movement and increase the risk for falls. Stoppages or freezing of gait involve both instabilities in posture and gait control as well as disruption of movement selection and planning, and thus such stoppages may reflect the breakdown of cortico-striatal communication, as opposed solely to losses of striatal dopamine.

Thus, the present invention relates to idalopirdine and an AChEI for use in the treatment of an elderly patient by reducing falls. The invention further relates to idalopirdine and an AChEI for use in the treatment of Parkinson's disease by reducing falls in a patient with Parkinson's disease. The invention also relates to a pharmaceutical composition comprising idalopirdine and an AChEI together with a pharmaceutically acceptable excipient.

According to the present invention, idalopirdine and an AChEI or a pharmaceutically acceptable salt of any of these two compounds may be administered in any suitable way, e.g. orally, transmucosally or parenterally, and idalopirdine and/or an AChEI may be presented in any suitable form for such administration. In one embodiment, and in accordance with the purpose of the present invention, idalopirdine and an AChEI are both administered in the form of solid pharmaceutical entities, suitably as tablets or capsules or in the form of suspensions, solutions or dispersions for injection.

The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 22 Edition, Hauber, Ed., Lippincott Williams & Wilkins, 2013. Tablets may thus be prepared by mixing the active ingredients with an ordinary carrier, such as an adjuvant and/or diluent, and subsequently compressing the mixture in a tableting machine.

Suitable pharmaceutical carriers and excipients include inert solid diluents or fillers, sterile aqueous solution and various organic solvents. Non-limiting examples of solid carriers are corn starch, lactose, terra alba, sucrose, cyclodextrin, talcum, gelatine, agar, pectin, acacia, magnesium stearate, stearic acid and lower alkyl ethers of cellulose. Non-limiting examples of liquid carriers are syrup, peanut oil, olive oil, phospholipids, fatty acids, fatty acid amines, polyoxyethylene and water.

Any other adjuvant or additive such as colorings, aroma, and preservatives may also be used provided that they are compatible with the active ingredients. The pharmaceutical compositions of the invention thus typically comprise an effective amount idalopirdine and/or an AChEI and one or more pharmaceutically acceptable carrier.

The pharmaceutical compositions formed by combining a compound used in the invention and the pharmaceutical acceptable carriers are then readily administered in a variety of dosage forms suitable for the disclosed routes of administration.

The active pharmaceutical ingredients used the present invention, i.e. idalopirdine and an AChEI, may be administered alone as pure compounds or in combination with pharmaceutically acceptable carriers or excipients, in either single or multiple doses.

The pharmaceutical compositions may be specifically formulated for administration by any suitable route such as the oral, rectal, nasal, pulmonary, topical (including buccal and sublingual), transdermal and parenteral (including subcutaneous, intramuscular and intravenous) route, the oral route being preferred. It will be appreciated that the administration route may depend on the general condition and age of the subject to be treated, the nature of the condition to be treated and the active ingredient chosen.

Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet. Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethyleneglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion. Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

When simultaneous administration of aidalopirdine and an AChEI is envisaged, a composition containing both idalopirdine and an AChEI may be particularly convenient. Alternatively, idalopirdine and an AChEI may be administered separately in the form of suitable compositions. The compositions may be prepared as described hereinabove. In one embodiment of the invention, separate unit forms of idalopirdine and an AChEI are administered simultaneously e.g. both compounds are administered with regular intervals once daily either morning or evening. In another embodiment, separate unit forms of idalopirdine and an AChEI are administered independently e.g. idalopirdine is administered with regular intervals once daily in the morning and the AChEI with regular intervals once daily in the evening or vice versa.

The present invention also comprises a kit comprising discrete unit dosage forms containing idalopirdine and discrete unit dosage forms containing an AChEI, all contained in the same container or pack, e.g. a blister pack.

Pharmaceutical compositions and kits according to the invention preferably comprises idalopirdine and an AChEI in therapeutically effective amounts. A daily dose of idalopirdine is preferably from 10 to 200 mg, such as from 10 mg to 120 mg, such as from 10 mg to 100 mg, such as from 30 mg to 90 mg, such as from 30 mg to 60 mg. A daily dose of donepezil is preferably from 1 mg to 30 mg, such as from 5 mg to 23 mg, such as 10 mg. A daily dose of rivastigmine is preferably from 1 mg to 20 mg. A daily dose of galantamine is preferably from 4 mg to 24 mg, such as from 8 mg to 24 mg, such as 8 mg, 12 mg, 16 mg, 20 mg or 24 mg.

Embodiments According to the Invention

In the following, embodiments of the invention are disclosed. The first embodiment is denoted E1, the second embodiment is denoted E2 and so forth.

E1. Idalopirdine and an AChEI for use in the treatment of an elderly patient by reducing falls.

E2. Idalopirdine and an AChEI for use in the treatment according to embodiment 1, wherein said elderly patient has been diagnosed with Parkinson's disease.

E3. Idalopirdine and an AChEI for use in the treatment of a CNS disease selected from the group consisting of Lewy Body Dementia (LBD), Parasupranuclear Palsy (PSP), Multi Systems Atropi (MSA) and Parkinson's disease, wherein the treatment of Parkinson's disease is selected from the group consisting of reducing falls in a patient with Parkinson's disease, improving low gait speed in a patient with Parkinson's disease, reducing movement stoppages in a patient with Parkinson's disease, reducing freezing gait in a patient with Parkinson's disease, and improving gait control in a patient with Parkinson's disease.

E4. Idalopirdine and an AChEI according to any of embodiments 1-3, wherein said AChEI is selected from donepezil, rivastigmine and galantamine.

E5. Idalopirdine and an AChEI for use in the treatment according to any of embodiments 1-4, wherein, when the AChEI is donepezil, the dose of donepezil is from 1 to 30 mg, such as from 5 to 23 mg; when the AChEI is galantamine, the dose is from 4 to 24 mg; and when the AChEI is rivastigmine, the dose of rivastigmine is from 1 to 20 mg.

E6. Idalopirdine and an AChEI for use in the treatment according to any of embodiments 1-5, wherein the daily dose of idalopirdine is from 10 mg to 120 mg, such as from 10 mg to 100 mg, such as from 30 mg to 90 mg, such as from 30 mg to 60 mg.

E7. Idalopirdine and an AChEI for use in the treatment according to any of embodiments 1-6, wherein said idalopirdine and said AChEI are administered simultaneously.

E8. Idalopirdine and donepezil for use in the treatment according to any of embodiments 1-6, wherein said idalopirdine and said AChEI are administered independently.

E9. Idalopirdine and donepezil for use in the treatment according to any of embodiments 1-8, wherein said idalopirdine and said AChEI are contained in separate unit dosage forms.

E10. Idalopirdine and donepezil for use in the treatment according to any of embodiments 1-7, wherein said idalopirdine and said AChEI are contained in the same unit dosage form.

E11. A method for the treatment of an elderly patient by reducing falls, the method comprising administration of therapeutically effective amounts of idalopirdine and an AChEI to a patient in need thereof.

E12. The method according to embodiment 11, wherein said elderly has been diagnosed with Parkinson's disease.

E13. A method for the treatment of a CNS disease selected from the group consisting of Lewy Body Dementia (LBD), Parasupranuclear Palsy (PSP), Multi Systems Atropi (MSA) and Parkinson's disease, wherein the treatment of Parkinson's disease is selected from the group consisting of reducing falls in a patient with Parkinson's disease, improving low gait speed in a patient with Parkinson's disease, reducing movement stoppages in a patient with Parkinson's disease, reducing freezing gait in a patient with Parkinson's disease, and improving gait control in a patient with Parkinson's disease, the method comprising administration of therapeutically effective amounts of idalopirdine and an AChEI to a patient in need thereof.

E14. The method according to any of embodiments 11-13, wherein said AChEI is selected from donepezil, rivastigmine and galantamine.

E15. The method according to any of embodiments 11-14, wherein, when the AChEI is donepezil, the therapeutically effective amount of donepezil is from 1 to 30 mg, such as from 5 to 23 mg; when the AChEI is galantamine, the dose is from 4 to 24 mg; and when the AChEI is rivastigmine, said therapeutically effective amount of rivastigmine is from 1 to 20 mg.

E16. The method according to any of embodiments 11-15, wherein said therapeutically effective amount idalopirdine is from 10 mg to 120 mg, such as from 10 mg to 100 mg, such as from 30 mg to 90 mg, such as from 30 mg to 60 mg.

E17. The method according to any embodiments 11-16, said idalopirdine and said AChEI are administered simultaneously.

E18. The method according to any embodiments 11-16, wherein said idalopirdine and said AChEI are administered independently.

E19. The method according to any of embodiments 11-18, wherein said idalopirdine and said AChEI are contained in separate unit dosage forms.

E20. The method according to any of embodiments 11-17, wherein said idalopirdine and said AChEI are contained in the same unit dosage form.

E21. Use of idalopirdine and an AChEI for the manufacture of a medicament for the treatment of an elderly patient by reducing falls.

E22. The use of idalopirdine and an AChEI according to embodiment 21, wherein said elderly has been diagnosed with Parkinson's disease.

E23. Use of idalopirdine and an AChEI for the manufacture of a medicament for the treatment of a CNS disease selected from the group consisting of Lewy Body Dementia (LBD), Parasupranuclear Palsy (PSP), Multi Systems Atropi (MSA) and Parkinson's disease, wherein the treatment of Parkinson's disease is selected from the group consisting of reducing falls in a patient with Parkinson's disease, improving low gait speed in a patient with Parkinson's disease, reducing movement stoppages in a patient with Parkinson's disease, reducing freezing gait in a patient with Parkinson's disease, and improving gait control in a patient with Parkinson's disease.

E24. The use of idalopirdine and an AChEI according to any of embodiments 21-23, wherein said AChEI is selected from donepezil, rivastigmine and galantamine.

E25. The use of idalopirdine and an AChEI according to any of embodiments 21-24, wherein, when the AChEI is donepezil, said medicament comprises from 1 to 30 mg, such as from 5 to 23 mg of donepezil; when the AChEI is galantamine, the dose is from 4 to 24 mg; and when the AChEI is rivastigmine, said medicament comprises from 1 to 20 mg of rivastigmine.

E26. The use of idalopirdine and an AChEI according to any of embodiments 21-25, wherein said medicament comprises idalopirdine in an amount from 10 mg to 120 mg, such as from 10 mg to 100 mg, such as from 30 mg to 90 mg, such as from 30 mg to 60 mg.

E27. A pharmaceutical composition comprising idalopirdine and an AChEI, together with a pharmaceutically acceptable excipient.

E28. The pharmaceutical composition according to embodiment 27, wherein said AChEI is selected from donepezil, rivastigmine and galantamine.

E29. The pharmaceutical composition according to any of embodiments 27-28, comprising from 30 mg to 60 mg of idalopirdine, wherein, when the AChEI is donepezil, said medicament comprises from 1 to 30 mg, such as from 5 to 23 mg of donepezil, when the AChEI is galantamine, said medicament comprises from 4 to 24 mg; and when the AChEI is rivastigmine, said composition comprises from 1 to 20 mg of rivastigmine.

E30. The pharmaceutical composition according to any of embodiments 27-28, comprising from 30 mg to 60 mg of idalopirdine.

E31. The pharmaceutical composition according to any of embodiments 27-30, for use in the treatment of an elderly patient by reducing falls.

E32. The pharmaceutical composition for use in the treatment according to embodiment 31, wherein said elderly patient has been diagnosed with Parkinson's disease.

E33. The pharmaceutical composition according to any of embodiments 27-30 for use in the treatment of a CNS disease selected from the group consisting of Lewy Body Dementia (LBD), Parasupranuclear Palsy (PSP), Multi Systems Atropi (MSA) and Parkinson's disease wherein the treatment of Parkinson's disease is selected from the group consisting of reducing falls in a patient with Parkinson's disease, improving low gait speed in a patient with Parkinson's disease, reducing movement stoppages in a patient with Parkinson's disease, reducing freezing gait in a patient with Parkinson's disease, and improving gait control in a patient with Parkinson's disease.

E34. A kit comprising idalopirdine and an AChEI.

E35. The kit according to embodiment 34, wherein said AChEI is selected from donepezil, rivastigmine and galantamine.

E36. The kit according to any of embodiments 34-35, which is adapted for simultaneous administration of said idalopirdine and said AChEI.

E37. The kit according to any of embodiments 34-35, which is adapted for independent administration of said idalopirdine and said AChEI.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the various aspects, embodiments, implementations and features of the invention mentioned herein may be claimed separately, or in any combination.

REFERENCES

1. Langston J W. The Parkinson's complex: Parkinsonism is just the tip of the iceberg. Ann Neurol 2006; 59(4):591-596.
2. Balash Y, Peretz C, Leibovich G, Herman T, Hausdorff J M, Giladi N. Falls in outpatients with Parkinson's disease: frequency, impact and identifying factors. J Neurol 2005; 252(11):1310-1315.
3. Wood B H. Incidence and prediction of falls in Parkinson's disease: a prospective multidisciplinary study. Journal of Neurology, Neurosurgery & Psychiatry 2002; 72(6):721-725.
4. Tinetti M E, Speechley M, Ginter S F. Risk factors for falls among elderly persons living in the community. N Engl J Med 1988; 319(26):1701-1707.
5. Baker S P, Harvey A H. Fall injuries in the elderly. Clin Geriatr Med 1985; 1(3):501-512.
6. Dellinger A M, Stevens J A. The injury problem among older adults: mortality, morbidity and costs. J Safety Res 2006; 37(5):519-522.
7. Cameron I D, Gillespie L D, Robertson M C, et al. Interventions for preventing falls in older people in care facilities and hospitals. Cochrane Database Syst Rev 2012; 12:CD005465.
8. Gillespie L D, Robertson M C, Gillespie W J, et al. Interventions for preventing falls in older people living in the community. Cochrane Database Syst Rev 2012; 9:CD007146.
9. Shen X, Wong-Yu I S, Mak M K. Effects of exercise on falls, balance, and gait ability in Parkinson's disease: A aeta-analysis. Neurorehabil Neural Repair 2015.
10. Chung K A, Lobb B M, Nutt J G, Horak F B. Effects of a central cholinesterase inhibitor on reducing falls in Parkinson disease. Neurology 2010; 75(14):1263-1269.
11. Henderson E J, Lord S R, Brodie M A, et al. Rivastigmine for gait stability in patients with Parkinson's disease (ReSPonD): a randomised, double-blind, placebo-controlled, phase 2 trial. Lancet Neurol 2016 [Epub ahrad of print].
12. van der Marck M A, Klok M P, Okun M S, et al. Consensus-based clinical practice recommendations for the examination and management of falls in patients with Parkinson's disease. Parkinsonism Relat Disord 2014; 20(4):360-369.
13. Montero-Odasso M, Verghese J, Beauchet O, Hausdorff J M. Gait and cognition: a complementary approach to understanding brain function and the risk of falling. J Am Geriatr Soc 2012; 60(11):2127-2136.
14. Ensrud K E, Blackwell T L, Mangione C M, et al. Central nervous system-active medications and risk for falls in older women. J Am Geriatr Soc 2002; 50(10):1629-1637.
15. Allcock L M, Rowan E N, Steen I N, Wesnes K, Kenny R A, Burn D J. Impaired attention predicts falling in Parkinson's disease. Parkinsonism Relat Disord 2009; 15(2):110-115.
16. LaPointe L L, Stierwalt J A G, Maitland C G. Talking while walking: Cognitive loading and injurious falls in Parkinson's disease. International Journal of Speech-Language Pathology 2010; 12(5):455-459.
17. Theill N, Martin M, Schumacher V, Bridenbaugh S A, Kressig R W. Simultaneously measuring gait and cognitive performance in cognitively healthy and cognitively impaired older adults: the Basel motor-cognition dual-task paradigm. J Am Geriatr Soc 2011; 59(6):1012-1018.
18. Brown L A, Shumway-Cook A, Woollacott M H. Attentional demands and postural recovery: the effects of aging. J Gerontol A Biol Sci Med Sci 1999; 54(4):M165-171.
19. Woollacott M, Shumway-Cook A. Attention and the control of posture and gait: a review of an emerging area of research. Gait Posture 2002; 16(1):1-14.
20. Hausdorff J M, Doniger G M, Springer S, Yogev G, Simon E S, Giladi N. A common cognitive profile in elderly fallers and in patients with Parkinson's disease: the prominence of impaired executive function and attention. Exp Aging Res 2006; 32(4):411-429.
21. Yogev-Seligmann G, Hausdorff J M, Giladi N. The role of executive function and attention in gait. Mov Disord 2008; 23(3):329-342.
22. Amboni M, Barone P, Hausdorff J M. Cognitive contributions to gait and falls: evidence and implications. Mov Disord 2013; 28(11):1520-1533.
23. Hasselmo M E, Sarter M. Modes and models of forebrain cholinergic neuromodulation of cognition. Neuropsychopharmacology 2011; 36(1):52-73.
24. Gritton H J, Howe W M, Mallory C S, Hetrick V L, Berke J D, Sarter M. Cortical cholinergic signaling controls the detection of cues. Proc Natl Acad Sci USA 2016; 113(8):E1089-1097.
25. Bohnen N I, Frey K A, Studenski S, et al. Gait speed in Parkinson disease correlates with cholinergic degeneration. Neurology 2013; 81(18):1611-1616.
26. Bohnen N I, Albin R L. Cholinergic denervation occurs early in Parkinson disease. Neurology 2009; 73(4):256-257.
27. Bohnen N I, Frey K A, Studenski S, et al. Extra-nigral pathological conditions are common in Parkinson's disease with freezing of gait: an in vivo positron emission tomography study. Mov Disord 2014; 29(9):1118-1124.
28. Bohnen N I, Müller M L T M, Koeppe R A, et al. History of falls in Parkinson disease is associated with reduced cholinergic activity. Neurology 2009; 73(20):1670-1676.
29. Yarnall A, Rochester L, Burn D J. The interplay of cholinergic function, attention, and falls in Parkinson's disease. Mov Disord 2011; 26(14):2496-2503.
30. Bohnen N I, Albin R L. The Cholinergic System and Parkinson Disease. Behav Brain Res. 2011; 221(2):564-573.
31. Kucinski A, de Jong I, Sarter M. Reduing falls in Parkinson's disease: Interactions between donepezil and the 5-HT$_6$ receptor antagonist idalopirdine on falls in a rat model of impaired cognitive control of complex movements. doi:10.1111/ejn.13354
32. Kucinski, A. et al. Modelling fall propensity in Parkinson's disease: Deficits in the attentional control of complex movements in rats with cortical-cholinergic and striatal-dopaminergic deafferentation. *J Neurosci*, 2013; 33, 16522-16539

EXAMPLES

Example 1 Reduction of Falls in DL Rats Treated with Donepezil and Idalopirdine

Materials and Methods
Subjects

Adult male and female Sprague Dawley rats (Harlan; N=70; 35 males and 35 females) between 3 and 6 months of age were individually housed in opaque single standard cages (27.70 cm×20.30 cm) in a temperature- and humidity-controlled environment (23° C., 45%). Throughout the experiment male rats weighed more than females (F(1,69) =460.29, P<0.001; males: 359.86+4.27 g females: 249.24+ 2.48 g), but weights did not differ across experimental groups (main effect of group and sex x group: both F<0.29, both P>0.88). The animals were maintained under a 12:12 hour light/dark schedule (lights on at 8:00 AM). Food (Rodent Chow; Harlan Teklad) was available ad libitum. Water access was gradually restricted over a 7-day period (12, 8, 5, 3, 1, 0.5, 0.25 hrs of water access per day) in the week before pre- and postsurgery behavioral testing. During testing, water was provided as rewards for correct responses during SAT performance and following beam traversals on the MCMCT (see below). Rats were also provided water ad libitum for 15 min following SAT performance each day.
Timeline of Experiments Animals were initially trained on the SAT (~2 months of daily training; ~9:00-11:00 AM). Upon reaching the final stage of training animals remained on this stage for 14 consecutive days. During the final 6 days of training rats were also trained on the MCMCT in the afternoons (~2:00-4:00 PM). Previous experiments showed that performance on either task was unaffected when rats were trained on both tasks on the same day. Furthermore, because we previously demonstrated that rats' circadian rhythm entrain to daily SAT practice, yielding a robust diurnal phenotype all behavioral testing likely occurred during the animals' active phase of the day.

Following pre-surgery training, animals underwent stereotaxic lesion surgeries followed by 4 weeks of recovery. During the final week of recovery animals were gradually water restricted. Drug effects were then assessed with 12 consecutive days of SAT and MCMCT sessions (see Table 1 for the battery of MCMCT test conditions):

TABLE 1

MCMCT testing sequence

| Day | Trial type | Rotating (10 rpm) | Distractor | Number of trials |
|---|---|---|---|---|
| Pre-Surgery Sequence | | | | |
| 1 | plank | | | 6 |
| 2 | plank | | | 6 |
| 3 | plank | | | 6 |
| 4 | rod | | | 6 |
| 5 | rod | | | 6 |
| 6 | rod | cc | | 6 |
| Post-Surgery Sequence | | | | |
| 1 | plank | | | 6 |
| 2 | rod | stationary | | 6 |
| 3 | rod | cc | | 6 |
| 4 | rod | cw | | 6 |
| 5 | rod | cc-cw-cc-cw-cc-cw | | 6 |
| 6 | rod | cc-cw-cc-cw-cc-cw | doorframe distractor | 6 (3 with doorframe) |
| 7 | rod | cc-cw-cc-cw-cc-cw | doorframe distractor | 6 (3 with doorframe) |
| 8 | rod | cc-cw-cc-cw | active distractor | 8 (4 shaping; 4 test trials) |
| 9 | rod | cc-cw-cc-cw | active distractor | 8 (4 shaping; 4 test trials) |
| 10 | rod | cc-cw-cc-cw-cc-cw-cc-cw-cc-cw | active distractor | 10 |
| 11 | rod | cc-cw-cc-cw-cc-cw-cc-cw-cc-cw | doorframe distractor | 10 (6 with doorframe) |
| 12 | rod | cc-cw-cc-cw-cc-cw-cc-cw-cc-cw | active distractor | 10 | cc, cw: counterclockwise, clockwise

Drug or vehicle injections were administered 30 minutes prior to SAT performance (~9:30 injections, SAT testing 10:00-10:45 a.m.) and in the afternoon before MCMCT testing (~3:30-6:00 p.m.). For the MCMCT runs, rats were injected individually so that trials began exactly 30 minutes after injection for each animal.
Lesions Of the 70 rats, 56 (28 females and 28 males) received dual striatal-dopaminergic, corticalcholinergic system lesions (DL) and were randomly assigned to 4 treatment conditions after surgeries (n=14/group, 7/sex). 14 rats (7/sex) received sham lesions. 6-OHDA was delivered bilaterally to dopamine terminals in the dorsal striatum (Sigma-Aldrich; 6.0 μg/2 μL/infusion, bolus; dissolved in 0.9% NaCl with 0.1% ascorbic acid; two infusion sites per hemisphere: AP+1.2 and +0.2 mm; ML ±2.5 and ±3.0 mm relative to bregma; DV −4.8 and −5.0 mm from skull). Desipramine hydrochloride (10 mg/kg; i.p.; Sigma-Aldrich) was administered to rats receiving 6-OHDA infusions 30 min prior to surgeries for protection of noradrenergic neurons[4]. Basal forebrain cholinergic neurons situated in the nucleus basalis and substantia innominate were targeted with immunotoxin 192 IgG-saporin (Advanced Targeting Systems) in aCSF infused bilaterally (120 ng/μL; 0.5 μL/hemisphere; AP −0.8; ML ±2.9; DV −7.8). Sham rats received equal volumes of 0.9% NaCl with 0.1% ascorbic acid (striatum) and aCSF (basal forebrain) without neurotoxins.
Michigan Complex Motor Control Task (MCMCT)

Complex movement performance measures including fall propensity were assessed using the MCMCT (for details and an illustration see Kucinski, A. et al (2013) Modelling fall propensity in Parkinson's disease: Deficits in the attentional control of complex movements in rats with cortical-cholinergic and striatal-dopaminergic deafferentation. J Neurosci, 33, 16522-16539). This beam traversal apparatus was designed to tax the ability of rats to perform attention demanding movements and correct for stepping errors while crossing a narrow square rod surface (2.54 cm2). The ends of the beam (2.0 m length) were held in sockets that allowed the rod to be rotated by a gear motor (10 RPM) coupled to one end of the beam element. Traversal of the rod, particularly when rotating, reliably generated falls and other movement impairments in rats with dual lesions of striatal dopaminergic and cortical cholinergic inputs. A flat plank surface (13.3 cm wide) was also used to assess basic motor capacity and for habituation to the apparatus. Two identical platforms (23.0×31.5 cm area) situated at the opposite ends of the beam were surrounded by retractable walls (27.0 cm height) to form end-box structures. The walls are raised and lowered manually and secured in position by a friction clamp which rides in a vertical slot in the support structure under the platform. The walls facing the beam had openings (9.0 cm wide) to allow rats to enter and leave the end-boxes. Copper water cups (2.7 cm diameter, 3 cm deep) were embedded on the floors of the end-boxes and rats were provided with ~150 µL of water following each traversal. These rewards were intended as an incentive for self-initiated traversals and thus limited experimenter handling during testing.

At the beginning of a test session, rats were placed on the rod or plank ~10 cm from an end-box and allowed to enter the box and drink the water rewards. Once inside the box on the first trial, and in subsequent trials, rats were given ~45 s to drink the water and explore. Rats were able to leave the end-boxes to traverse to the opposite side of the beam at any time. If after 45 s the rats did not initiate traversal, the walls were lowered as cues to begin traversal. The majority of rats self-initiated traversal when the walls were lowered, however, if not, the rats were moved to the plank or rod by the experimenter. When falls occurred, animals fell into a safety net (0.7×0.2 m) section of a badminton net (generic) placed 20 cm below the beam element. The net frame also served as a mounting point for the various cameras, mirrors, and distractor elements.

Falls, slips, and traversal time were assessed as described in Kucinski, A. et al (2013) Modelling fall propensity in Parkinson's disease: Deficits in the attentional control of complex movements in rats with cortical-cholinergic and striatal-dopaminergic deafferentation. *J Neurosci*, 33, 16522-16539). A fall was scored in the following instances: when slip/missteps caused a rat to stop forward movement and lose upright walking posture resulting in the underside of the animal hitting the surface of the rod, when the rat fell completely off the rod onto the netting below the rod or hung from the rod by its paws, when a rat ceased forward movement and clung to the rod while it rotated (thus rotating upside down with it), or when a rat ceased forward movement and sat perpendicularly on the rod for greater than 2 s while attempting but failing to resume forward movement. A slip was scored when any of the rats' paws lost contact with the surface of the rod and extended below the lower horizontal border of the rod. Traversal time was defined as the latency to traverse the entire distance of the beam. During trials in which a fall occurred, slips and traversal time were prorated by multiplying the ratio of the distance of a full traversal to the distance where the hind limbs lost contact with the rod during the fall.

Two distractors were presented during traversals. First, a passive doorframe distractor, comprised of a 46.0×39.4 cm surface with a door-frame shape cutout of 20 cm×10 cm made of foam core, was incorporated into the MCMCT test sequence. The distractor was placed at the midway point along the beam (100 cm mark) with side jambs 3.5 cm from the rod surface on both sides and the top border of the doorframe cutout 11 cm above the flat rod surface. We previously found that this distractor caused movement disruptions such as freezing of gait and falls, therefore modeling the effects of such distractor in PD patients. Second, animals were tested with an active distractor task in which a water reward (3 drops of water; ~150 µL) was presented on a platform (4.9 cm diameter) during traversals. The platform was also placed at the 100 cm mark, with 2-3 cm separating the rod and the platform.

Rats were first acclimated to the task in 4 shaping trials (test days 8 and 9). In these trials rats were placed directly on the stationary (non-rotating) rod adjacent to the platform (approximately midway across the beam) and allowed to drink the water from the platform. After shaping trials, rats underwent 4 test trials in which the rats performed unassisted traversals of the rotating rod (alternating directions) with presentations of water rewards. In two other test days (10 and 12), rats performed 10 test runs per day. In addition to falls, the number of water rewards earned, defined as licking/drinking water from the platform for ≥1 sec, were counted. All trials were recorded using a system of 4 bullet cameras (KT&C; model KPCS190SH Black/White Bullet Camera with ⅓" SONY Super HAD CCD) with rotatable bases that were fastened to the outer support frame of the outer side of the apparatus by hand clamps. Performance measures were analyzed by video playback by experimenters blind to the lesion status and treatment regimen of the rats Sustained Attention Task (SAT)

Apparatus.

Training and testing were conducted using 12 operant chambers (MED Associates Inc.) housed within individual sound-attenuating cubicles. Each chamber was equipped with two retractable levers, a central panel white light (2.8 W), and a water dispenser located on the same wall as the panel lights. The water dispenser was capable of administering 45 µL of water per delivery. Signal presentation, lever operation, reinforcement delivery, and data collection were controlled by a Pentium PC and Med-PC for Windows software (version 4.1.3; MED Associates).

Acquisition.

Water-deprived rats were initially trained to press a lever for a water reward in accordance with a modified fixed ratio-1 (FR1) schedule for water reinforcement. During this phase of training, any lever press resulted in the delivery of water. Typically, the animals do not exhibit a side bias with regard to which lever is pressed; however, if one lever was pressed 5 times in succession, the FR1 schedule was modified to require the animal to press the opposite lever before the next reward can be obtained. After 3 consecutive days with 120 reinforced lever presses each, the rats began training to discriminate between a signal (1 s illumination of the central panel light) and a non-signal (no illumination) event. Two seconds (5) after a signal or nonsignal event, both levers were extended into the operant chamber and remain extended for 4 s or until a lever was pressed. If no press occurred after 4 s, the levers retracted and an omission was scored. Immediately following responses (either correct or incorrect), both levers were retracted and the variable intertrial interval (ITI; 12±3 s) was reset. On signal trials, a press of the left lever was reinforced and termed a "hit," whereas a press of the right lever was not reinforced and termed a "miss." On non-signal trials, a press of the right lever was reinforced and termed a "correct rejection," whereas a press of the left lever was not reinforced and termed a "false alarm."

Animals received water rewards only for correct responses (45 µL for each hit and correct rejection), whereas incorrect responses (misses and false alarms) were not rewarded. To eliminate the possibility of a selection bias, half of the animals were trained with the opposite pattern. Signal and non-signal events were presented in pseudorandom order for 81 trials each (total of 162 trials) per session. During this phase of training, incorrect responses were followed by correction trials in which the previous trial was repeated. After three consecutive incorrect responses on correction trials, the animal underwent a forced trial in which the lever was extended for 90 s or until the animal made a response. If the forced choice trial was a signal trial, the signal light remained illuminated for as long as the lever was extended. The house light was not illuminated during this training stage. Animals progressed to the subsequent step of shaping if they responded correctly to ≥70% of both signal and non-signal trials for 3 consecutive days.

During the third phase of shaping, multiple signal durations (500, 50, and 25 ms) were introduced and the ITI was reduced to 9±3 s. Correction and forced-choice trials were also eliminated. Trial type and signal duration were pseudorandomly determined for each trial. Session length was set at 40 min. After at least 3 d of stable performance, defined by at least 70% hits to 500 ms signals, 70% correct rejections, and ≤30% omissions, animals began training in the final version of the task. The final version was identical to the previous training stage except that the house light was illuminated throughout the session. The addition of the illuminated house light represents a crucial element of testing sustained attention as it requires the animal to constrain its behavior and focus on the central panel light during task performance. Upon reaching the final stage of training prior to lesion surgeries, animals remained at this stage for 14 consecutive days and scores from the final 5 days of performance were averaged to determine pre-surgery scores for each animal. During post-surgery testing of drug effects, rats were tested only on the final stage for 12 consecutive days and scores from the final 5 days were once again averaged for final analyses.

Measures of SAT Performance.

The following behavior measures were recorded during each SAT session: hits, misses, false alarms, correct rejections, and omissions. Misses and false alarms are the inverse of hits and correct rejections, respectively. The relative number of hits (hits/hits+misses) for each signal length as well as the relative number of correct rejections (correct rejections/correct rejections+false alarms) were calculated. In addition, an overall measure of attentional aptitude, the SAT score, that integrates both the relative number of hits (h) and the relative number of false alarms (f), was also determined at each signal duration. The SAT score was calculated using the following formula: $(h-f)/[2(h+f)-(h+f)^2]$. Thus, SAT scores are not confounded by errors of omission. SAT scores ranged from 1.0 to −1.0, with 1.0 indicating that all responses were hits and correct rejections, 0 indicating an inability to discriminate between signal and non-signal events, and −1.0 indicating that all responses were misses and false alarms. Errors of omission were recorded separately.

Histology and Assessments of Lesions

Following the completion of post-surgery drug testing, rats were deeply anesthetized and transcardially perfused at a rate of 50 mL/min with 0.1M phosphate buffer solution (PBS) for 2 minutes followed by perfusion with 4% paraformaldehyde in 0.4M Na-phosphate solution and 15% picric acid (pH 7.4) for 9 minutes. Brains were rapidly removed and postfixed for 2-6 h at 4° C. and then rinsed in 0.1M PBS and stored in 30% sucrose solution and allowed to sink. Coronal sections (40 µM thickness) were sliced using a freezing microtome (CM 2000R; Leica) and stored in antifreeze solution. Tyrosine hydroxylase (TH) and ChAT immunostains were performed as described in literature.

TH-immunostained sections were imaged at 4× magnification using a Leica DM400B digital microscope. SPOT 5.1 software (Spot Imaging Solutions) was used to capture images. Two sections (AP+1.2 and +0.2 mm) were used to generate a single score depicting the size and degree of bilateral lesions. 6-OHDA infusions were targeted to the dorsal striatum centered between the medial and lateral boundaries. The lesion size was rated based on the size of the area of TH loss observed in the dorsal striatum, with a score of 10 corresponded to 100% of the dorsal striatum exhibiting TH loss, a score of 5 to 50%, and a score of 1 to 10%. The extent of TH clearance (degree of TH loss) within the lesion size area was also determined based on a scale of 1-10, with a rating of 10 corresponding to complete depletion of TH within the lesion space, and lower values corresponding to the percent of TH remaining (example: 5 is 50% TH loss, 2 is 20% TH loss). Scores for lesion size and extent were averaged from both sections and hemispheres to yield a single lesion score for each rat.

To assess the extent of cholinergic cell losses, semi-quantitative estimates of the number of cholinergic neurons were generated as done previously. Photographs of the ChAT-stained basal forebrain of the two hemispheres were taken at 5× magnification using a Leica DM400B digital microscope. Cell count estimates were taken from the area of the nucleus basalis of Meynert (nbM) and substantia innominata (SI) within a 680 µm×680 µm region, and from the horizontal nucleus of the diagnonal band/preoptic area within a 1000 µm×1300 µm region. The "count" function Photoshop CS6 was used to quantify the number of ACh cells. This feature also tags each neuron already counted to prevent double-counts and allows for review by a second counter. These semi-quantitative estimates from the two hemispheres were averaged to yield a single estimate per rat. To determine relationships between the degree of lesions and measures of performance and to verify similar lesions between DL lesion groups, a single composite core, reflecting the severity of the two system lesions, was generated for each rat. For this purpose, cholinergic cell loss of two basal forebrain areas per hemisphere were rated from 5 to 1 (5: >90% cell loss relative to control; 4: >80%; 3: >70%; 2: >60%; 1: >30-50% loss). This score multiplied by 2 was averaged with the TH lesion score described above to generate a single composite score (out of 10) per DL rat.

Drug Administration and Doses

Donepezil and idalopirdine were dissolved in 5% 2-hydroxypropyl-beta-cyclodextrin vehicle solution. Rats were divided into the following drug administration groups (14 per group, 7 per sex): sham-lesioned and administered vehicle (SH/VEH), DL and vehicle (DL/VEH), DL and donepezil (DL/DON), DL and idalopirdine (DL/IDL), and DL and idalopirdine plus donepezil (DL/DON+IDL). Solutions were prepared the night before administration and were replaced every 6 days. DON and IDL were dissolved in the same solution for the combination treatment. Rats were injected s.c. (2.0 mL/kg) at four alternating injection sites (left neck, right flank, right neck, left flank; sequence repeated). Rats were injected 30 minutes prior to performing the SAT in the morning and 30 minutes prior to performing the MCMCT in the afternoon.

Drug doses were selected based on data from a pilot experiment that assessed, in 4 DL rats each, the effects of DON alone, at 0.1, 0.3, and 1.0 mg/kg, or administered in combination with IDL (5.0 mg/kg). Results suggested that MCMCT performance of DL rats may benefit most clearly from the treatment combination involving the middle dose of DON.

Statistical Analyses

SAT and MCMCT performance measures were compared between the five groups and primarily using within-subjects repeated-measures ANOVAs as well as one or two-way ANOVAs when applicable. Sex was a factor in all analyses. The analysis of SAT scores and hits also included the within-subject factor signal duration (500, 50, and 25 ms). For MCMCT runs on the rod (test days 2-5), traversal time, slips and falls were assessed using condition (stationary, rotating counterclockwise (cc) or clockwise (cw), or rotating in alternating directions) as a within-subjects factor. For each condition (or day), performance measures were averaged over each rats' 6 runs on that day and these averaged values were used for statistical analyses. On doorframe test days (6, 7, and 11), falls evoked by the doorframe distractor were compared between groups and sexes. Falls and rewards obtained during the active distractor condition were compared using two way ANOVAs. Comparisons of doorframe evoked-freeze behavior and other performance measures between DL/VEH and DL/DON+IDL rats were carried out using two-way ANOVAs. Two-way ANOVAs were also used to compare TH/ChAT composite lesion scores between the drug groups and sexes. Following significant main effects, post hoc multiple comparisons were conducted using the Least Significant Difference (LSD) test. Significant interactions between the effects of group and other factors were followed by one-way ANOVAs on the effects of group and LSD multiple comparison tests. Statistical analyses were performed using SPSS for Windows (version 17.0: SPSS). In cases of violation of the sphericity assumption, Huyhn-Feldt-corrected F-values, along with uncorrected degrees of freedom, are given. Alpha was set at 0.05. Exact P values are reported as recommended previously. Variances are reported and illustrated as standard error of the mean (SEM). Effect sizes for selected effects are reported using Cohen's d.

Results

Pre-Surgery SAT and MCMCT Performance

Prior to surgery, rats underwent SAT training until they reached stable criterion performance and they were also familiarized with the MCMCT.

DON+IDL Reduced Fall Rate in DL Rats

On the first day of postsurgery MCMCT testing (Table 1) rats traversed the plank surface. This surface rarely causes slips or falls and thus only traversal time was assessed. Traversal time did not differ between groups and sexes (main effects and interaction: all $F<1.46$, all $P>0.23$; 4.02±0.16 s per traversal).

On days 2, 3, 4 and 5 rats performed traversals with the rod surface and were assessed for traversal time as well as slips and falls (6 traversals per day, 24 total runs). On day 2 the rod remained stationary (non-rotating) followed by rotation of the rod (10 RPM) in the familiar counterclockwise (cc) direction on day 3. On day 4 the rod's direction was reversed to the unfamiliar clockwise (cw) direction and on day 5 the direction of rotation was alternated between successive trials (cc-cw-cc-cw-cc-cw). Performance measures were analyzed for the effects of group, sex, and testing condition (stationary rod, cc, cw, alternating) as the within-subjects factor.

Falls.

Traversing the rotating rod generally increased the number of falls across all animals (main effect of testing condition: $F(3,180)=6.48$, $P<0.001$; falls from stationary rod: 21.67±1.90%, rotating counterclockwise (cc): 32.62±1.90%, clockwise (cw): 30.00±2.34%, alternating: 30.00±2.00%; less falls on stationary rod than all other conditions; all $P<0.001$). Across these trials, a main effect of group on fall frequency ($F(4,60)=2.62$, $P=0.04$) reflected that compared with the frequency of falls in DL/VEH rats, SH/VEH and DL/DON+IDL rats fell significantly less frequently (Cohen's d=0.96; for multiple comparisons see FIG. 1A). Furthermore, and in contrast to DL/DON+IDL rats, with a fall frequency that was statistically similar to that seen in SH-VEH rats, rats treated only with IDL fell as frequently as untreated DL rats (DL/VEH). The frequency of falls in DL/DON rats tended to be lower than in DL/VEH rats but the effect did not reach significance (P=0.17). The effects of group and testing condition did not interact ($F(12,180)=1.00$, $P=0.45$) indicating that performance across all rod conditions contributed to the effect of DON+IDL (FIGS. 1B-1D). There was no sex effect and no interactions involving sex (all $F<1.69$, all $P>0.17$).

Traversal Speed.

Similar to the Effects on Falls, Traversal Speed Differed Between Groups ($F(4,60)=3.31$, $P=0.02$), with the treatment group that fell as often as vehicle-treated DL rats, DL/IDL, exhibiting the slowest traversals (SH/VEH: 3.96±0.19 s; DL/VEH: 4.62±0.25 s; DL/DON: 4.48±0.36 s; DL/IDL: 5.48±0.45 s, DL/DON+IDL: 4.58±0.32 s; DL/IDL significantly slower than all other groups). Moreover, males were generally slower than females $F(1,60)=13.54$, $P=0.001$; males: 5.12±0.23 s, females: 4.13±0.17 s. In either sex, body weights were not correlated with traversal speeds (both $R2<0.06$). Traversal speed was not affected by testing condition and no 2- or 3-way interactions between the 3 factors were found (all ($F<0.91$, $p>0.33$).

Slips.

Traversing rotating rods generally caused more slips compared with the stationary rod ($F(3,180)=37.53$, $P<0.001$; stationary: 1.02±0.67 slips; cc: 2.31±0.16; cw: 2.39±0.15; alternating: 2.35±0.13). The number of slips did not differ among groups ($F(4,60)=2.37$, $P=0.06$), with the trend reflecting that DL/IDL rats appeared to slip more frequently than all other DL rats (SH/VEH: 1.60+0.11; DL/VEH: 2.04+0.16; DL/DON: 2.04+0.14; DL/IDL: 2.51+0.38, DL/DON+IDL: 1.92+0.16). Males slipped more often than females ($F(1,60)=5.64$, $P=0.02$; males: 2.24±0.17; females: 1.79±0.10) but once again there were no interactions between the three factors (all $F<1.01$, $p>0.44$). Slips in males, but not females were positively correlated with their body weights (males: R2=0.14, P=0.03; females: R2=0.08, P=0.10).

Reduced Doorframe-Associated Falls in DON+IDL-Treated DL Rats

In PD patients who already have a propensity for freezing of gait, tight doorways are highly effective in evoking freezing and thus increasing the risk for falls. This effect is hypothesized to reflect a shift of limited attentional resources away from supporting forward movement to the processing of this passive distractor. The doorframe distractor (FIG. 2A) was placed along the rod on test days 6, 7 and 11.

Overall, the door distractor more than tripled the percentage of trials in which falls occurred ($F(1,60)=117.10$, $P<0.001$; door falls: 38.34±2.89%, non-door falls: 11.30±1.34%). The main effect of group ($F(4,60)=3.24$, $P=0.018$) and a significant door x group interaction ($F(4,60)=3.15$, $P=0.02$) reflected that doorframe-evoked falls accounted for the group differences (FIG. 2B). DL rats treated either with VEH, DON or IDL experienced more doorframe-associated falls than SH/VEH rats. In contrast, in the presence of the doorframe, fall rates in DL/DON+IDL rats did not differ from those in SH/VEH rats and were significantly lower than fall rates in DL/IDL rats (Cohen's d=0.74; FIG. 2B). In all rats, the rate of doorframe-associated falls decreased across the three testing days (main effect of day: $F(1,120)=48.31$, $P<0.001$; day 1: 64.76±4.42% falls, 2: 38.10±4.14%, 3: 12.14±2.14; all interactions with other factors: $F<1.34$, $P>0.23$).

The doorframe caused almost twice as many falls in males than females, however males did not fall more than females in the absence of the doorframe (sex x condition: $F(1,60)=34.24$, $P<0.001$; percentage of door falls over trials; females: 25.69±3.76%, males: 50.99±3.22%, t(69)=26.09, $P<0.001$; non-door falls females: 13.27±1.81%, males: 9.32±1.95%, t(69)=2.20, $P=0.14$). Doorframe-associated falls in males did not correlate with their body weights or traversal speeds (both $R2<0.03$). However, slower females had more falls in this condition ($R2=0.21$, $P=0.005$). There were no significant interactions between the 3 factors (all $F<1.31$, all $P>0.25$).

Microbehavioral Correlates

To determine potential behavioral correlates of the DON+IDL treatment effect on doorframe-associated falls, a video-based analysis of the animals' microbehavior during doorframe traversal was conducted. Doorframe runs from DL/VEH and DL/DON+IDL male and female rats from days was selected when their fall rates reflected their group means (days 6 and 7 for females, and 11 for males). In general, it was observed that the rats of both groups stopped forward movement when approaching the doorframe (effects of groups on freezing duration: $F(1,27)=1.22$, $P=0.28$; DL/VEH: 1.25±0.22 s/freeze; DL/DON+IDL: 0.93±0.21 s). Furthermore, the individual rats' duration of freezing periods correlated with their fall rates (FIG. 2C). Because longer freezes nearly consistently were associated with falls in all rats, doorframe-evoked freezes were grouped into long (≥2 s) versus short freezes (<2 s). The percentage of trials in which a long freeze occurred did not differ between the two groups (6 trials per animal; $F(1,27)=2.59$, $P=0.12$; 26.79±4.95% of trials involved long freezes). In addition, rates of falls associated with long freezes—in animals that displayed at least one such freeze (10 DL/VEH and 9 DL/DON+IDL)—did not differ between these two groups ($F(1,18)=0.004$, $P=0.95$; DL/VEH: 62.67±12.62% falls in runs involving long doorframe-associated freezes; DL/DON+IDL: 63.89±13.89%). However, fall rates associated with short freezes were higher in DL/VEH than the DL/DON+IDL rats (14 rats per group; $F(1,27)=5.27$, $P=0.03$, FIG. 2D). Thus, these observations indicated that treating DL rats with DON+IDL did not increase the proportion of doorframe runs that were associated with relatively short freezes, but DON+IDL-treated rats were more capable of resuming an continuing the traversal after short freezes.

To further detail the potential effects of the combined treatment with DON+IDL, representative runs were selected (first two trials on doorframe day 2 in females and on day 3 for males; 2 trials per rat) the rate of the following behaviors was counted for a 1-s period beginning shortly after and during short freezes (0.5-1.5 s of freezing periods): (1) sudden increases of traversal speed after a freeze; (2) high and firm tail position while passing under the doorframe associated with controlled, upright posture and forward focus in contrast to a low, dragging tail and slouched posture and downward focus typical of DL rats; 31 (3) swinging of the tail to maintain balance following doorframe-associated slips; (4) the use of forelimbs to 'push' the upper trunk of the body back onto the rod after slips; (5) active hind limb movements ('walking in place') during freezes to maintain balance on the rod; and (6) small 'hops' after freezes to reestablish forward momentum through the doorframe. Results indicate that, first, a composite score collapsing counts of all 6 behaviors negatively correlated with fall rates in both groups (both $R^2>0.42$, both $P<0.02$), indicating that active recovery movements following short freezes are a strong predictors of successful doorframe runs. Second, DL/DON+IDL rats exhibited more instances of category #2 behavior (above) than DL/VEH rats ($X^2=7.22$, $P=0.03$, DL/VEH: 0.18±0.10 counts/trial, DL/DON+IDL: 0.54±0.11; all other categories of behavior: $P>0.30$; FIG. 2E).

Lack of Treatment Effects on Active Distractor-Associated Falls

Falls in aged humans and PD patients are correlated with poor dual task performance. To model the impact of the reallocation of attentional resources to a secondary task on complex movement control, water-deprived rats were offered water for retrieval while traversing the rotating rod.

Overall, 54 of the 70 (77.14%) animals retrieved water (defined as licking water for at least 1 s, regardless of falls) in at least one trial (13 SH/VEH, 9 DL/VEH, 10 DL/DON, 11 DL/IDL, and 11 DL/DON+IDL; 26 males and 28 females). A main effect of group indicated that all DL rats retrieved water less frequently than SH/VEH rats ($F(4,60)=3.32$, $P=0.016$) although multiple comparisons indicated that DL/DON rats' retrieval count was not significantly lower than DL/VEH (FIG. 3B). Females retrieved water more frequently than males ($F(1,60)=10.56$, $P=0.002$; females: 49.78±6.32%, males: 26.69±4.36%], however the effects of sex did not interact with group ($F(4,60)=1.50$, $P=0.22$). In this test, water retrievals and falls are confounded measures as stopping forward movement to retrieve water is a high risk for falls. SD/VEH rats succeeded more frequently in retrieving water without falling than DL rats ($F(4,60)=5.84$, $P<0.001$; FIG. 3C). Furthermore, females successfully retrieved water without falling more frequently than males ($F(1,60)=10.81$, $P=0.002$; females 33.98+5.02% of trials; males: 16.73+3.36%) but this effect did not interact with group ($F(1,69)=1.56$, $P=0.19$). In neither sex did this measure correlate with body weights, traversal speed or doorframe-associated falls all $R2<0.1$). Thus, DL lesions reduced the engagement with the active distractor and increased associated fall rates, but the drug treatments did not benefit rod traversal performance in the presence of this active distractor.

Lack of Treatment Effects on SAT Performance

Following the completion of the postsurgery recovery period of four weeks, animals were returned to morning SAT and afternoon MCMCT testing, and drug treatments were administered 30 min prior to the morning as well as the afternoon test session. DL lesions impaired SAT performance. However, none of the treatments improved performance.

Example 2: Reduction of Falls in DL Rats Treated with Rivastigmine and Idalopirdine Study Outline:

Dual lesion (DL) or sham operated rats were treated subcutaneously (s.c.) with either vehicle (10% 2-hydroxypropyl-β-cyclodextran; 2-HPBCD, in saline), 1 mg/kg rivastigmine, 10 mg/kg idalopirdine or a combination of the two treatments for 10 subsequent days at a volume of 5 ml/kg. Statistical comparisons were made with a one-way ANOVA and a post hoc Dunnetts's multiple comparison test with DL vehicle treated animals as the control.

MCMCT: Deviations of the Apparatus from Example 1:

The apparatus was similar to that used previously (Kucinski et al., 2013). It consisted of a 3 meter long (2.54 cm2) straight square rod or a zigzag rod with two bent surfaces along the rod, supported between two one meter long towers on which the start and end platforms were held. These identical platforms were 30 cm×25 cm and each consisted of a 3 cm diameter copper water cup embedded in the floor. The platforms were surrounded by retractable wall structures which were 23 cm high when in the fully raised positions. These walls could be raised and lowered mechanically by a 12 VDC electric motor controlled remotely by a toggle switch, and thus allowed conversion from an open platform to start and a box structure to end. On the wall facing the beam there was a 9 cm wide opening to allow rats access to and from the beam. The rod was made of aluminum tubing enclosed in gray gaffer's tape used for traction. For plank conditions, a 13.3 cm wide plank was placed directly on top of the rod and fitted inside the edges of the support towers. A 12 VDC electric motor was used to rotate the rod, controlled by a pulse width modulator. 20 cm underneath the rod, a safety net was suspended to catch the rats during falls. Recordings of the MCMCT were taken using 4 bullet Marshall 1080-HD-DI model CV500 Series cameras (B-30/25P frame rate/59.94i) mounted on a frame parallel to one side of the rod. The videos were converted to a single feed using a quad SDI to HDMI multiviewer (Matrox Micro-Quad) and viewed directly on a PC using Elgato Game Capture HD software.

TABLE 2

MCMCT Sequence

| Day | Trial Type | Condition | Distractor | Number of Trials |
|---|---|---|---|---|
| Pre-surgery | | | | |
| 1 | Plank | | | 6 |
| 2 | Rod | Stationary | | 6 |
| 3 | Rod | Rotating (cc; 10 rpm) | | 6 |
| Post-surgery | | | | |
| 1 | Plank | | | 6 |
| 2 | Rod | Stationary | | 6 |
| 3 | Rod | Rotating (cc; 10 rpm) | | 6 |
| 4 | Rod | Rotating (cw; 10 rpm) | | 6 |
| 5 | Rod | Rotating (alt; 10 rpm) | | 6 |
| 6 | Rod | Rotating (alt; 10 rpm) | Doorframe | 6 (4 with doorframe) |
| 7 | Rod | Rotating (alt; 10 rpm) | Doorframe | 6 (4 with doorframe) |
| 8 | Rod (zigzag) | Stationary | | 6 |
| 9 | Rod (zigzag) | Rotating (slow; 5 rpm) | | 6 |
| 10 | Rod (zigzag) | Rotating (fast; 8 rpm) | | 6 | cc: counterclockwise, cw: clockwise, alt: alternating cc/cw

Results:

The results are shown in FIGS. 4-7, and it can be observed that the combined treatment of DL rats with idalopirdine and rivastigmine (DL/Riva+IDL) reduced the number of falls compared to the untreated DL rats (DL/Veh).

What is claimed is:

1. A method of treating an impairment of cognitive control of balance, gait or movement caused by a CNS disease, wherein said method comprises administering a therapeutically effective amount of a 5-$HT_6$ receptor antagonist in combination with an acetylcholinesterase inhibitor to a subject suffering from impairment of cognitive control of balance, gait or movement due to degeneration of, or functional impairment in, cholinergic neurons, and wherein said CNS disease is selected from the group consisting of: Parkinson's Disease, Lewy Body Dementia, Parasupranuclear Palsy and Multi-Systems Atrophy.

2. The method of claim 1, wherein said CNS disease is Parkinson's Disease.

3. The method of claim 2, wherein said treatment reduces the number or severity of falls of said subject, improves low gait speed in said subject, reduces movement stoppages in said subject, reduces freezing gait in said subject, or improves gait control in said subject.

4. The method of claim 1, wherein said 5-$HT_6$ receptor antagonist is idalopirdine.

5. The method of claim 4, wherein said idalopirdine is administered at a dose of from 10 mg to 120 mg.

6. The method of claim 1, wherein said acetylcholinesterase inhibitor is selected from the group consisting of donepezil, rivastigmine, and galantamine.

7. The method of claim 6, wherein said 5-$HT_6$ receptor antagonist is idalopirdine.

8. The method of claim 6, wherein when said acetylcholinesterase inhibitor is donepezil, said donepezil is administered at a dose of from 1 to 30 mg; when said acetylcholinesterase inhibitor is galantamine, said galantamine is administered at a dose of from 4 to 24 mg; and when said acetylcholinesterase inhibitor is rivastigmine, said rivastigmine is administered at a dose of from 1 to 20 mg.

9. The method of claim 8, wherein said 5-$HT_6$ receptor antagonist is idalopirdine.

10. The method of claim 9, wherein said idalopirdine is administered at a dose of from 10 mg to 120 mg.

11. The method of claim 8, wherein said 5-$HT_6$ receptor antagonist is idalopirdine and said acetyl cholinesterase inhibitor is donepezil.

12. The method of claim 11, wherein said treatment reduces the number or severity of falls by a subject with Parkinson's Disease.

13. The method of claim 11, wherein said treatment improves low gait speed in a subject with Parkinson's Disease.

14. The method of claim 11, wherein said treatment reduces movement stoppages in a subject with Parkinson's Disease.

15. The method of claim 11, wherein said treatment reduces freezing gait in a patient with Parkinson's Disease.

16. The method of claim 15, wherein said freezing gait is of less than about 2 seconds.

17. The method of claim 11, wherein said treatment improves gait control in a patient with Parkinson's Disease.

* * * * *